May 21, 1974

E. CULLEY

Plant Pat. 3,551

BALD CYPRESS

Filed Dec. 27, 1971

United States Patent Office

Plant Pat. 3,551
Patented May 21, 1974

3,551
BALD CYPRESS

Earl Cully, R.R. 5, Jacksonville, Ill. 62650

Filed Dec. 27, 1971, Ser. No. 212,828
Int. Cl. A01h *7/00*
U.S. Cl. Plt.—50 1 Claim

ABSTRACT OF THE DISCLOSURE

This disclosure concerns a new and distinct variety of Gymnospermae, Pinaceae (Taxodiaceae), commonly known as a bald cypress, characterized by its rapid straight growth of its central trunk, abundant production of lateral primary branches extending at an angle of branching 40 to 45 degrees below vertical and second or tertiary branching usually at increasing angles from the top of the tree downward giving a fuller than usual crown, and the relatively short branches resulting in a tightly pyramidal crown.

BACKGROUND OF THE INVENTION

This new variety of bald cypress was discovered by me in east central Johnson County in Illinois on cultivated property where it had grown to a height of 70 feet. During the past several years, I have grafted many cuttings from this parent tree to other *Taxodium distichum* root stocks. At present, I have over 1,000 grafts and all are growing true to form in the Cully Nursery in Jacksonville, Illinois.

DESCRIPTION OF THE NEW PLANT VARIETY

Figure 2:
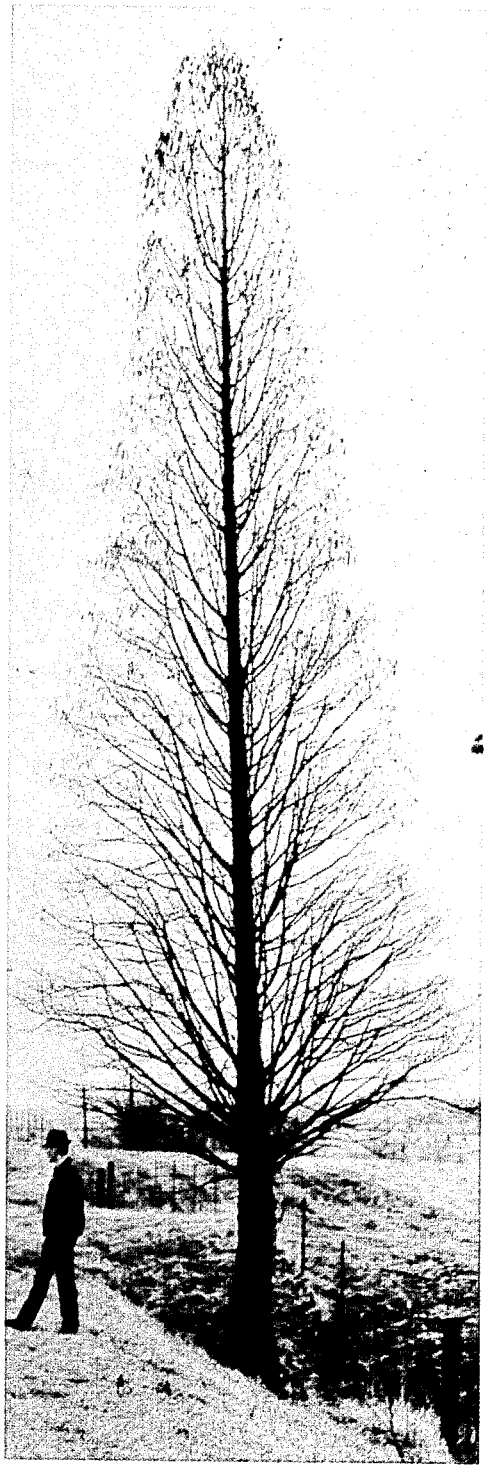
FIG. 2 shows my new variety without leaves.
Figure 1:
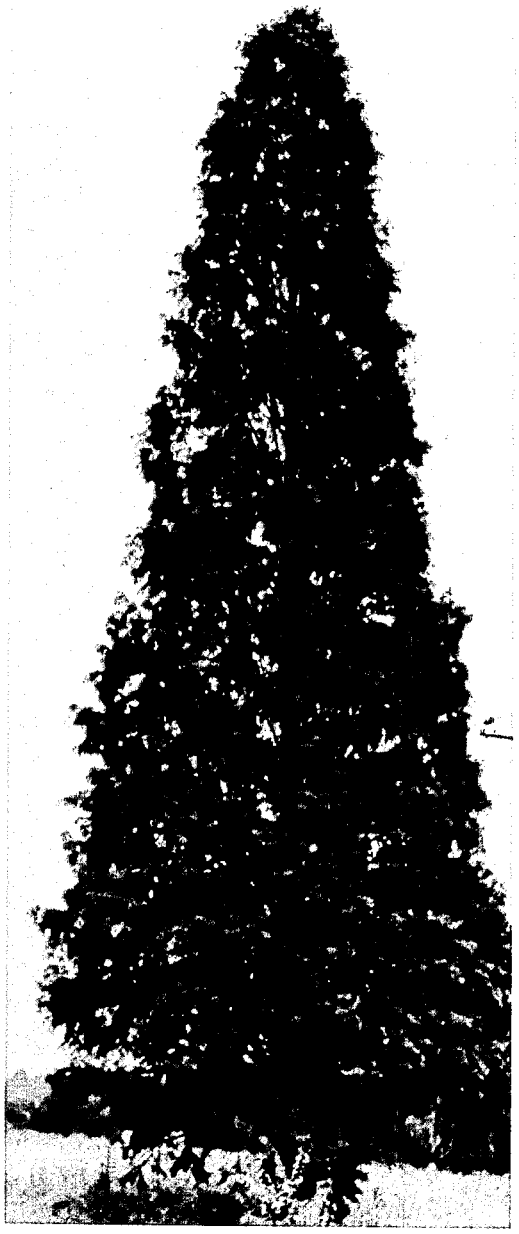
FIG. 1 shows my new variety in full leaf.

The following is a detailed description of my new variety of Bald Cypress.

Origin: Seedling.
Parentage: Unknown.
Classification: Gymnospermae, Pinaeceae (L.).
*Botanic.—Taxodium distichum* (L.).
Form: Tree.
Shape: Tightly pyramidal.
Height: 70 feet.
Trunk Size: 26 inches in diameter at breast height at full growth; 36 inches in diameter at ground level at full growth.
Growth Rate: Rapid, with a limb spread of about 18 feet at full growth.

Branches:
*Angle of attachment.*—40 to 45 degrees below vertical.
*Spacing.*—Dense (18 to 24 inches apart).
*Size.*—Relatively small to 9 feet long.
Leaves:
*Length.*—1 to 1.5 centimeters on deciduous branches; two ranked, alternate lanceolate, apiculate.
Flowers: Male and female strobiles.
*Blooming period.*—March and April in Illinois, typical for species.
Fruit: A cone typical of the species.

This new variety most resembles *Metasequoia glyptostroboides* "National," an unpatented variety in a related genus of the Taxodiaceae, in tree outline but is differentiated therefrom by the rapid straight growth of its central trunk with a limb spread of 18 feet, an abundant production of lateral primary branches with the angle of branching extending 40 to 45 degrees below vertical for the primary branches, the tertiary branches branching usually at an increasing angle from the top of the tree downwardly giving a fuller than usual crown, and the shorter branches producing a tightly pyramidal crown.

I claim:

1. A new and distinct variety of bald cypress tree Gymnospermae, Pinaceae (Taxodiaceae) as shown and described, characterized particularly as to novelty by the rapid straight growth of its central trunk, with a limb spread of 18 feet, abundant production of lateral primary branches, with the angle of branching extending 40 to 45 degrees below vertical for the primary branches, and tertiary branching usually at increasing angles from the top of the tree downward giving a fuller than usual crown, and the relatively short branches producing a tightly pyramidal crown.

References Cited

The First Plant Patents, Allyn, Educ. Found. Inc., 1934, pp. 67–69 relied on.
The Standard Cydo., Bailey, 1935, pp. 3314 relied on.
Trees for Amer. Gardens, Wyman, 1951, p. 327 relied on.
New Illus. Ency. of Gard., Everett, 1960, p. 2249 relied on.
Manual of . . .Rehder, 1960, p. 49 relied on.

ROBERT E. BAGWILL, Primary Examiner